US006576422B1

(12) United States Patent
Weinstein et al.

(10) Patent No.: US 6,576,422 B1
(45) Date of Patent: Jun. 10, 2003

(54) METHOD FOR IDENTIFYING PRODUCTS EMPLOYING GENE EXPRESSION

(75) Inventors: Barry Weinstein, Dresher, PA (US); Lorraine Holowach Keller, Lansdale, PA (US); Subba Reddy Palli, Lansdale, PA (US)

(73) Assignee: Rohm and Haas Company, Philadelphia, PA (US)

( * ) Notice: Subject to any disclaimer, the term of this patent is extended or adjusted under 35 U.S.C. 154(b) by 0 days.

(21) Appl. No.: 09/690,391

(22) Filed: Oct. 17, 2000

(51) Int. Cl.[7] .............................. C12Q 1/68; C12Q 1/02; C12P 1/00; G01N 33/566; A01H 5/00
(52) U.S. Cl. ............................. 435/6; 435/29; 435/41; 435/172.1; 435/172.3; 435/320; 436/501; 800/303; 800/271; 800/274
(58) Field of Search ................................. 435/6, 29, 41, 435/172.1, 172.3, 320, 69.7; 436/501; 800/303, 271, 274, 278

(56) References Cited

U.S. PATENT DOCUMENTS

| 4,954,655 | A |   | 9/1990  | Kelly .......................... 564/464 |
| 4,985,461 | A |   | 1/1991  | Hsu et al. ..................... 514/615 |
| 5,071,773 | A | * | 12/1991 | Evans et al. ...................... 435/6 |
| 5,429,952 | A |   | 7/1995  | Garner et al. ................. 436/518 |
| 5,514,578 | A |   | 5/1996  | Hogness et al. .......... 435/240.2 |
| 5,530,028 | A |   | 6/1996  | Lidert et al. ................. 514/649 |
| 6,013,836 | A |   | 1/2000  | Hsu et al. ..................... 564/149 |
| 6,025,483 | A | * | 2/2000  | Yanofsky .................... 536/23.6 |
| 6,147,282 | A | * | 11/2000 | Goff et al. .................... 800/303 |
| 6,245,531 | B1 |  | 6/2001  | Hogness et al. ............. 435/69.7 |
| 6,258,603 | B1 |  | 7/2001  | Carlson et al. ............... 435/468 |

FOREIGN PATENT DOCUMENTS

| EP | 0327163 B1 | 4/1995 |
| EP | 0949269 A1 | 10/1999 |
| WO | WO 87/06383 | 10/1987 |
| WO | WO 95/02823 | 1/1995 |
| WO | WO 97/35985 | 10/1997 |
| WO | WO 98/33162 | 7/1998 |
| WO | WO 99/10510 | 3/1999 |
| WO | WO 99/27365 | 6/1999 |
| WO | WO 99/51777 | 10/1999 |
| WO | WO 1/61350 A1 | 8/2001 |

OTHER PUBLICATIONS

Olie et al., "Application of the CALUX bioassay system . . . ", Organohalogen compounds, vol. 27, pp. 280–284, 1996.*
Brennan, Journal of Fluorescence, 9:295–312, 1999.
Fields, et al. A novel genetic system to detect protein–protein interactions, Nature 340: 245–246, 1989.
Yao T–P, et al. Functional ecdysone receptor is the product of ECR and ultraspiracle genes, Nature 366: 476–479, 1993.

* cited by examiner

Primary Examiner—W. Gary Jones
Assistant Examiner—Arun Kr. Chakrabarti
(74) Attorney, Agent, or Firm—Camille Jolly-Tornetta; Thomas D. Rogerson; Rachel H. Rondinelli

(57) ABSTRACT

A method for identifying a product involves the steps of: (1) associating with the product a marker ligand; and (2) detecting the marker ligand in the product at a later point in time as a means of identifying the product by contacting the product with a detector composition. The detector composition comprises one or more first nucleotide sequences encoding one or more natural or synthetic ligand-dependent transcription factors, wherein said factors comprise at least one ligand binding domain, at least one DNA binding domain and at least one transactivation domain; and a second nucleotide sequence encoding a reporter gene under the regulatory control of a receptor response element or a modified or synthetic response element, and a second promoter. The method may also employ a corepressor or coactivator or a nucleotide sequence encoding the corepressor or activator Interaction between the marker ligand and ligand binding domain is highly specific and induces a change in the expression of the reporter gene, the change producing a detectable signal identifying the presence of the marker ligand in the product. The detector composition, a cell line containing the first and second nucleotide sequences, kits using them and products marked with specific marker ligands are useful in this method.

44 Claims, No Drawings

METHOD FOR IDENTIFYING PRODUCTS EMPLOYING GENE EXPRESSION

FIELD OF THE INVENTION

The present invention relates generally to the field of product identification; and more specifically, to the application of biotechnological systems to mark products for identification.

Background of the Invention

The interaction between a variety of ligands and the receptors with whiche they bind intracellularly has been exploited in fields where the triggering of a receptor-induced promoter enables the promoter-regulated expression of a gene encoding a desired protein. Such inducible expression systems permit the desired protein to be produced in the cell at an appropriate timepoint. One such receptor system is the insect steroid hormone receptor system disclosed in U.S. Pat. No. 5,514,578.

Such systems are used in drug or new compound screening. For example, International patent application No. WO092/27356, published Jun. 3, 1999, refers to methods for identifying modulators of nuclear hormone receptor function by mixing the receptor, a peptide sensor, and a test compound. The sensor provides direct binding to the receptor, and an assay is performed to determine if the test compound influenced the binding of the sensor protein to the receptor. Additionally, Evans, U.S. Pat. No. 5,071,773 refers to hormone receptor related bioassays as screens to determine whether proteins are receptors that activate transcription or whether a test agent is a ligand that activates a known receptor.

Such receptor systems have been proposed for "fingerprinting" or as biosensors for marking products for identification. For example, the interaction between certain G-protein coupled cell surface receptors, tyrosine canasta receptors, and ion channel receptors which have been mutated to have altered binding to their natural ligands and various non-natural ligands thereto, have been proposed for the generation of a sample fingerprint. The fingerprint is proposed to enable the authentification and monitoring of products for safety, security, fraud and quality control. See, International Patent Application No. WO99/51777, published Oct. 14, 1999; and International Patent Application No. WO97/15985, published Oct. 2, 1997. International Patent Application No. WO95/0282, published Jan. 26, 1995 refers to a method of detecting a ligand by incubating cells transfected with DNA coding for a receptor that can influence cell amplification in response to the ligand, with a test substance that is a potential agonist or antagonist of the receptor. A marker for amplification in the cells is then used to assess the presence or absence of amplification of cells.

Some disadvantages of these prior art detection systems include a need for light concentration of ligand in the marked product as well as a limitation on the number and character of the ligands that can be used in the detection method.

There is a need in the art for additional uses of receptor-ligand interactions for product identification which interactions can generate simple and rapid signals at low concentrations.

Summary of the Invention

In one aspect, the present invention provides an improved method for identifying a product, which employs ligand-dependent transcription factors. This method involves first associating a marker ligand with the product, and then detecting the marker ligand in the product or a portion or extract thereof at a later point in time as a means of identifying the product. The ligand-containing product is contacted with a detector composition comprising one or more first nucleotide sequences encoding one or more natural or synthetic ligand-dependent transcription factors. The ligand-dependent transcription factor(s) comprise at least one ligand binding domain, at least one DNA binding domain and at least one transactivation domain. The factor(s) are preferably under the regulatory control of a first promoter. The detector composition also comprises a second nucleotide sequence encoding a reporter gene under the regulatory control of a receptor response element or a modified or synthetic response element, and a second promoter. The interaction between the marker ligand and at least one of the ligand binding domains is highly specific and induces a change in the expression of the reporter gene. This change produces a detectable signal identifying the presence of the ligand in the product.

In another aspect, the invention provides an additional method such as that described above, but wherein the detector composition further comprises a third nucleotide sequence encoding a coactivator or corepressor that interacts with the ligand-dependent transcription factor to activate or repress expression of said reporter gene. In still another embodiment of a method of this invention, the product is contacted with the detector composition and either a coactivator or repressor protein that interacts with the ligand-dependent transcription factor to activate or repress expression of said reporter gene.

In another aspect, the invention provides a marked product comprising a liquid, a solid, a dispersion, an emulsion, or a latex associated with a specified marker ligand described in detail below.

In a further aspect, the invention provides one or more cells or a stable cell line comprising the above-described first nucleotide sequence(s) and the above-described second nucleotide sequence, and optionally the coactivator or corepressor for use in the claimed method.

In still another aspect, the invention provides a kit for identifying a marked product comprising a detector composition comprising the above-described first and second nucleotide sequences, and means for detecting and measuring the signal.

In yet another aspect, the invention provides detector compositions for such use.

Other aspects and advantages of the present invention are described further in the following detailed description of the preferred embodiments thereof.

DETAILED DESCRIPTION OF THE INVENTION

A The present invention provides methods and compositions that employ natural or synthetic ligand-dependent transcription factors that participate in receptor-ligand interactions that enable rapid and efficient product identification. The methods and compositions of this invention generate simple and rapid signals at low concentrations, and are thus safe and suitable for application to many products and industries.

This invention provides a novel method for identifying a product. According to this method, a product is first associated with a marker ligand. The presence and/or quantity of marker ligand in or on the product, or in or on an extract or portion of the product, is detected at a later point in time as a means of identifying the source of the product and/or validating the authenticity of the product. Detection of the marker ligand is made by using an "in vivo"step, i.e., by contacting the product with a detector composition that comprises one or more first nucleotide sequence(s) that encodes one or more natural or synthetic ligand-dependent transcription factor(s), optionally under the regulatory control of a first promoter. These transcription factors contain three functional regions: a ligand binding domain, a DNA binding domain and a transactivation domain. Another portion of this detector composition is a second nucleotide sequence encoding a reporter gene that is under the regulatory control of a receptor response element or a modified or synthetic response element and a second promoter. Interaction between the marker ligand and at least one of the ligand binding domains is highly specific and induces a change in the expression of the reporter gene. That change in the reporter gene thereby produces a detectable signal identifying the presence of the ligand in the product. More specifically, the binding of the marker ligand to the ligand binding domain in the detector composition triggers the binding of the DNA binding domain to the response element. When the response element becomes bound, it activates or suppresses the expression of the reporter gene. Optionally, a coactivator or corepressor protein or a nucleotide sequence encoding same is added to the method or to the detector composition.

One advantage of the method of this invention over those of the above-mentioned references include high specificity for artificial small molecule marker ligands, which are nonhazardous when present in consumer products. Additionally the specificity between the ligand binding domains and the ligands results in a very low potential for interference in this method. The marker ligands are also easy to synthesize and manufacture. Additionally, unlike other marker systems, the present invention can use many markers. Further, this method is highly sensitive, and can detect very low concentrations of marker ligand in a product, e.g., at parts per billion (ppb) to parts per trillion (ppt) levels. In fact, concentration of marker ligands can be so low in this method that the concentrations cannot be detected by conventional chemical chromatographic or mass spectrometry methods. Finally, in contrast to the known methods, cell proliferation in this biological method of marker detection is independent of the presence of marker ligand.

To understand this invention fully, the following components, defined as follows, are used:

A. The Product

As used in the methods and compositions of this invention, a "product" to which one or more marker ligands is added, may be any type of product for which identifiable marking is desirable, so to ascertain the source of the product. For example, such "marking"may be necessary to police unlicensed or illegal duplication of the product or for other security purposes, or to enable the identification of an adulterated product for reasons of consumer safety. The product may be in any physical form. For example, the product may be a fluid or liquid, a solid, or some intermediate therebetween, such as a dispersion, an emulsion, a latex, or a semi-solid matrix.

Examples of typical solid products can include, without limitations pharmaceutical tablets, capsules and powders; solid formulations of agrochemicals such as insecticides, herbicides, fungicides, fertilizers, other agricultural chemicals, and seeds; explosives; textiles such as clothing; recordings such as gramophone records, tape cassettes, floppy discs and compact discs; elelectrical goods such as television sets, computers and radios; motor vehicle components and cameras; paper such as documents, confidential papers, notes, securities, labels, and packaging; chemical products such as inks, biocides, and rubbers; cosmetics such as creams; food products; and construction materials, such as asphalt additives, roof shingles, and concrete blocks, as well as packaging materials.

Examples of fluid or liquid products include, without limitation, oil-based products such as lubricating oils, hydraulic oils, greases, gasoline. kerosene, crude petroleum, diesel fuel, and liquified petroleum products, gasahol, biodiesel fuel, motor oil transmission fluid; paints, paint additives, plastic additives, adhesives, coatings,. ceramics; oil-field chemicals, including polymers; perfumes and other cosmetics; drinks such as bottled water milk, wine, whisky, sherry, gin and vodka and other alcoholic and non-alcoholic beverages; liquid pharmaceutical formulations such as syrups, emulsions and suspensions: water treatment chemicals, such as polymers, scale inhibitors, and chelating agents; liquid agrochemical formulations, such as pesticides, insecticides, and herbicides; and industrial solvents. The product is preferably liquid.

One of skill in the art may readily select the product to which a marker ligand is to be introduced, according to this invention without any unnecessary experimentation. It will be appreciated that the marker ligand, described in detail below, may be associated with the product in a wide variety of ways. Thus the marker ligand may be present in or on all or part of the product, or in or on all or part of a label, wrapper or container associated with the product.

Preferably, the marker ligand is directly admixed into the product, e.g., where the product is a fluid, or semi-solid, or even a powder. Where the product is a solid, the marker ligand may be present independently of the product, for example, the marker ligand may be present in the product packaging, tags or labels. Alternatively, where the product is a solid, the marker ligand may be applied to the surface of the product and dried. Methods of application of the marker ligand to a solid product may include without limitation, roller transfer or paint coating, spray coating, brush coating and dip coating. The application method must be applied so that drying takes place on the product at a selected temperature, e.g., room temperature or greater than room temperature. General descriptions of these types of coating methods may be found in conventional texts, such as *Modern Coating and Drying Techniques*, (E. Cohen and E. Gutoff, eds; VCH Publishers) N.Y. (1992) and *Web Processing and Converting Technology and Equipment*, (D. Satas, ed; Van Nostrand Reinhold) N.Y. (1984).

In one embodiment, the marker ligand is present in a product at a concentration of between I parts by trillion (ppt) to about 500 parts per billion (w/w) of marker ligand. In another embodiment, the marker ligand is present in the product at a concentration of between 0.1 ppb to about 100 ppb of marker ligand. In yet another embodiment, the marker ligand is present in a product at a concentration of between about 0.1 to 10 ppb of ligand.

According to the method of this invention, the presence of marker ligand in or on the product may be detected by examining the entire product, a portion (e.g. a small quantity) of the product, or an extract of the product (e.g., such as where the product is a solid).

The selection of the product and product form, the method of incorporation of the marker ligand into or on the selected product, and the amount of marker ligand to be associated with the product are not limitations on the present invention, but are variables that may be readily selected by the person of skill in the art in view of the teachings provided herein.

B. Marker Ligands

The marker ligands useful in the present invention include molecules that specifically bind to the ligand binding domain of a natural or synthetic ligand-dependent transcription factor. The marker ligand can specifically interact with at least one of the selected ligand binding domains. Preferably, the marker ligand is a synthetic chemical compound or composition which demonstrates preferential specific binding to the ligand binding domains described in detail below. The marker ligand is not normally present in the product; for example, it is not a by-product of the production process, normal impurity, or standard additive for that product. Another advantage of the marker ligands useful in this invention is that the marker ligands are inert in the sense that they do not react with the product which they label.

Preferred marker ligands useful in this invention include known compounds, or compounds readily synthesized by one of skill in the art, as disclosed in U.S. Pat. Nos. 4,954,655; 4,985,461; 5,117,057; 5,530,028; 5,378,726; and 6,013,836. These patents are incorporated by reference herein for the purpose of defining certain chemical compounds useful as marker ligands in this invention. Thus the marker ligand may include, without limitation, ponasterone, ponasterone A, muristerone A, an alkylhydrazin, an N,N'-diacylhydrazine, an N-substituted-N, N' diacylhydrazine, an N-substituted-N,N'-disubstituted hydrazine, a dibenzoylalkyl cyanohydrazine, an N-alkyl-N,N'-diaroylhydrazine, an N-acyl-N- alkyl-N'-aroylhydrazine, a 3 ,5-di-tert-butyl-Y-hydroxy-N-isobutyl-benzamide, an 8-O-acetylharpagide. In embodiments in which the ligand binding domain is derived, for example, from the ecdysone nuclear receptor, a variety of alkylhydrazilles, N-substituted-N,N'-diacylhydrazines, and N-substituted-N,N'-disubstituted hydrazines may be employed as the marker ligands [see, e.g., U.S. Pat. Nos. 4,954,655; 4,985,461; 5,530,028;), and 6,013,836]. A particularly preferred marker ligand which is used in the following examples is N '-tert-butyl-N'-(3 ,5-dimethylbenzoyl)-3-methoxy-2-methylbenzohydrazide, which is informally referred to as methoxyfenoxide.

Still other suitable compounds useful as marker ligands are disclosed in pending U.S. patent application Ser. No. 09/315,451, which is also incorporated by reference herein. One such marker ligand is defined by the formula:

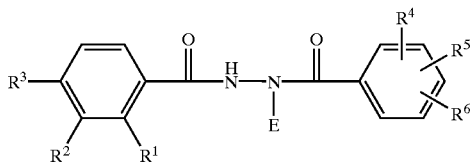

wherein:

E is a $(C_4-C_6)$alkyl containing a tertiary carbon or a cyano$(C_3-C_5)$alkyl containing a tertiary carbon;

$R^1$ is H, Me, Et, i-Pr, F, formyl, $CF_3$, $CHF_2$, $CHCl_2$, $CH_2F$, $CH_2Cl$, $CH_2OH$, $CH_2OMe$, $CH_2CN$, CN, C≡CH, 1-propynyl, 2-propynyl, vinyl, OH, OMe, OEt, cyclopropyl, $CF_2CF_3$, CH≡CHCN, allyl, azido, SCN, or $SCHF_2$; $R^2$ is H, Me, Et, n-Pr, i-Pr, formyl, $CF_3$, $CHF_2$, $CHCl_2$, $CH_2F$, $CH_2Cl$, $CH_2OH$, $CH_2OMe$, $CH_2CN$, CN, C≡CH, 1-propynyl, 2-propynyl, vinyl, Ac, F, Cl, OH, OMe, OEt, O-n-Pr, OAc, $NMe_2$, $NEt_2$, SMe, SEt, $SOCF_3$, $OCF_2CF_2H$, COEt, cyclopropyl, $CF_2CF_3$, CH≡CHCN, allyl, azido, $OCF_3$, $OCHF_2$,F O-i-Pr, SCN, $SCHF_2$, SOMe, NH-CN, or joined with $R^3$ and the phenyl carbons to which $R^2$ and $R^1$ are attached to form an ethylenedioxy, a dihydrofuryl ring with the oxygen adjacent to a phenyl carbon, or a dihydropyryl ring with the oxygen adjacent to a phenyl carbon;

$R^3$ is H, Et, or joined with $R^2$ and the phenyl carbons to which $R^2$ and $R^3$ are attached to form an ethylenedioxy, a dihydrofuryl ring with the oxygen adjacent to a phenyl carbon, or a dihydropyryl ring with the oxygen adjacent to a phenyl carbon: $R^4$, $R^5$ and $R^6$ are independently H, Me, Et, F, Cl, Br, formyl, $CF_3$, $CHCl_2$, $CHCl_2$, $CH_2F$, $CH_2Cl$, $CH_2OH$, CN, C≡CH, 1-propynyl, 2-propynyl, vinyl, OMe, OEt, SMe, or SEt;

provided that:

a) when $R^1$ is Me and $R^2$ is OMe; then $R^3$ is H and the combination $R^4$, $R^5$, and $R^6$ is 3,5-di-Me, 3,5-di-OMe-4-Me, 3,5-di-Cl, or 2,5-di-F;

b) when $R^1$ is Me and $R^2$ is OEt; then $R^3$ is H and the combination $R^4$, $R^5$, and $R^6$ is 3,5-di-Me, 3,5-di-OMe-4-Me, 3,5-di-CI, 3,5-di-F, 2,4-or 2,5-di-F:, 2,4-or 2,5-di-Cl;

c) when $R^1$ is Et and $R^2$ is OMe or OEt; then $R^3$ is H and the combination $R^4$, $R^5$, and $R^6$ is:
i) 3,5-di-OMe-4-Me, 3,5-di-Cl, 3.5-di-l:, 2,4-or 2.5-di-F, 2,4-or 2,5-di-Cl, 3-OMe, 2-Cl-5-Me, 2-Br-5-Me, 2-Cl, 2-Br, or 3-Me; or
ii) $R^6$ is H, $R^4$ is Me, and $R^5$ is Et, F, Cl, Br, formyl, $CF_3$, $CHF_2$, $CHCl_2$, $CH_2F$, $CH_2Cl$, $CH_2OH$, CN, C≡CH, 1-propynyl, 2-propynyl, vinyl, OMe, OEt, SMe, or SEt;

d) when $R^1$ is i-Pr; then $R^2$ is OMe, or OEt; $R^3$ is H; and the combination $R^4$, $R^5$, and $R^6$ is 3,5-di-Me;

e) when $R^3$ is Et; then $R^2$ is H, $R^1$ is F or Cl, and the combination $R^4$, $R^5$, and $R^6$ is 3,5-di-Me;

f) when $R^2$ and $R^3$, together with the phenyl carbons to which they are attached, form an ethylenedioxy ring; then $R^1$ is Me or Et and the combination $R^4$, $R^5$, and $R^6$ is 3,5-di-Me;

g) when $R^2$ and $R^3$, together with the phenyl carbons to which they are attached, form a dihydrofuryl or dihydropyryl ring; then $R^1$ is Et and the combination $R^4$, $R^5$, and $R^6$ is 3,5-di-Me;

h) when $R^1$ is formyl, $CF_3$, $CHF_2$, $CHCl_2$, $CH_2F$, $CH_2Cl$, $CH_2OH$, $CH_2OMe$, $CH_2CN$, CN, C≡CH , 1-propynyl, 2-propynyl, vinyl, OH, cyclopropyl, $CF_2CF_3$, CH≡CHCN, allyl, azido, SCN, or $SCHF_2$; then $R^2$ is OMe or OEt, $R^3$ is H, and the combination $R^4$, $R^5$, and $R^6$ is 3,5-di-Me; and i) when $R^2$ is Me, Et, n-Pr, i-Pr, formyl, $CF_3$, $CHF_2$, $CHCl_2$, $CH_2F$, $CH_2Cl$, $CH_2OH$, $CH_2OMe$, $CH_2CN$, CN, C≡CH, 1-propynyl, 2-propynyl, vinyl, Ac, F, Cl, OH, O-n-Pr, OAc, $NMe_2$, $NEt_2$, SMe, SEt, $SOCF_3$, $OCF_2CF_2H$, COEt, cyclopropyl, $CF_2CF_3$, CH≡CHCN, allyl, azido, $OCF_3$, $OCHF_2$, O-i-Pr, SCN, $SCHF_2$, SOMe, or NH-CN; then $R^1$ is Et, $R^3$ is H, and the combination $R^4$, $R^5$, and $R^6$ is 3,5-di-Me.

One particularly desirable marker ligand has the above specified formula in which E is t-butyl; $R^1$ is Me, Et, i-Pr, or F; $R^2$ is OH, OMe, OEt, or joined with $R^3$ and the phenyl carbons to which $R^2$ and $R^3$ are attached to form an ethylenedioxy or dihydrofuryl ring with the oxygen adjacent to a phenyl carbon; $R^3$ is H, Et or joined with $R^2$ and the phenyl carbons to which $R^2$ and $R^3$ are attached to form an ethylenedioxy or dihydrofuryl ring with the oxygen adjacent to a phenyl carbon; and $R^4$, $R^5$, and $R^6$ are independently Me, F, Cl, $CH_2OH$, or OMe. Another desirable ligand has the above-specified formula, in which E is t-butyl; $R^1$ is Me, Et, i-Pr, or F; $R^2$ is OH, OMe, OEt, or joined with $R^3$ and the phenyl carbons to which $R^2$ and $R^3$ are attached to form an ethylenedioxy or dihydrofuryl ring with the oxygen adjacent to a phenyl carbon; $R^3$ is H, Et or joined with $R^2$ and phenyl carbons to which $R^2$ and $R^3$ are attached to form an ethylenedioxy or dihydrofuryl ring with the oxygen adjacent to a phenyl carbon; and $R^4$, $R^5$, and $R^6$ are independently Me, F, Cl, $CH_2OH$, or OMe.

Still another marker ligand has the above-specified formula in which E is t-butyl; $R^1$ is Me, Et, i-Pr, or F; $R^2$ is OH, OMe, OEt, or joined with $R^3$ and the phenyl carbons to which $R^2$ and $R^3$ are attached to form an ethylenedioxy or dihydrofuryl ring with the oxygen adjacent to a phenyl carbon; $R^3$ is H. Et or joined with $R^2$ and the phenyl carbons to which $R^2$ and $R^3$ are attached to form an ethylenedioxy or dihydrofuryl ring with the oxygen adjacent to a phenyl carbon; and $R^4$, $R^5$, and $R^6$ are independently Me, F, Cl, $CH_2OH$, or OMe. Other marker ligands may be selected from the specified formula by one of skill in the art.

These compounds as marker ligands are particularly desirable, because they are nonhazardous at the concentrations which would be present in consumer products, such as pharmaceuticals, cosmetics, foods, packaging, etc. Further, very small concentrations of such ligands in a product, e.g., in the range of parts per billion to parts per trillion, call be detected and quantified by the method of this invention.

One of skill in the art may use molecules in addition to the molecules described above as marker ligands, provided that the marker ligand binds at least one of the selected ligand binding domain(s) of a natural or synthetic ligand-dependent transcription factor of the detector composition, as described below.

C. Detector Composition

A detector composition of the present invention refers to a composition which comprises one or more "first" nucleotide sequences that encode one or more natural or synthetic ligand-dependent transcription factors. The factor(s) are preferably under the regulatory control of a first promoter. The composition also contains a "second" nucleotide sequence encoding a reporter gene that is under the regulatory control of a receptor response element or a modified or synthetic response element, and a second promoter. Optionally, the detector composition contains a "third" nucleotide sequence encoding a coactivator or corepressor. These nucleotide sequences may be RNA or DNA. In one embodiment, the DNA sequences making up the detector composition are preferably incorporated into a cell or cells. More preferably, the detector composition containing the nuclcotide sequences is a stable cell or cell line.

The cell(s) of the detector composition can be any eukaryotic or prokaryotic cell(s). Of the eukaryotic cells, invertebrate cells (such as insect cells) are preferred because they confer the most sensitive response to the market ligands of the preferred receptors, e.g., the ecdysone receptor. The selection of other cell and receptor combinations may be made by one of skill in the art in view of this disclosure. Thus, the ligands of this invention will have negligible physiological or other effects on transformed cells, or the whole organism. Therefore, cells can grow and express the desired product, substantially unaffected by the presence of the ligand itself. Preferably, in a eukaryotic cell, the nucleotide sequences of the detector composition are located in the nucleus.

In one preferred embodiment, the detector composition containing the two nucleotide sequences is an insect cell or cells, such as *Spodoptera frugiperda* (Sf9). Insect cells tend to be very sensitive and robust in tolerating numerous receptors for use in this composition. Other insect cells include the insect cell line, BRL-AG2, derived from cotton boll weevil, *Anthomus grandis* as described in Stiles el al, *In Vitro Cell Dev. Biol.,* 28A: 355–363 (1992). Another insect cell line L57 derived from the *Drosophila melanogaster* Kc cell line may also be employed. Still other insect cells for use in this composition may be selected by one of skill in the art.

In another preferred embodiment, the detector composition is a yeast cell or cells, such as *Saccharomyces cerevisiae*. In another preferred embodiment, the detector composition is *Pichia pastoris*. Still another preferred yeast cell for use in this invention is *Pichia methanolica*. Still other strains of yeast cells for use in this invention include, without limitation, a wide variety of strains of Sacccharomyces Candida, Ambrosiozyma, Apiotrichum, Arthroascus, Hansenula, Kloeckera, Kluyveromyces, Pichia, Rhodosporidium, Rhodotorula, Schizosaccharomyes, and Torulaspora.

For example, in one embodiment, the detector composition is a mammalian cell. Desirable mammalian cells include, without limitation, cells such as CHO, BHK, MDCK, and various murine cells, e.g., 10T1/2 and WEHI cells, African green monkey cells, suitable primate cells, e.g., VERO, COSI, COS7, BSCI, BSC 40, and BMT 10, and human cells such as W138, MRC5, A549, human embryonic retinoblast (HIER), human embryonic kidney (HEK), human embryonic lung (HEL), TH1080 cells. Other suitable cells may include NIH3T3 cells (subline of 3T3 cells), HepG2 cells (human liver carcinoma cell line), Saos-2 cells (human osteogenic sarcomas cell line), HuH7 cells or HeLa cells (human carcinoma cell line). In one embodiment, appropriate cells include the human embryonic kidney 293T cells. Neither the selection of the mammalian species providing the cells nor the type of mammalian cell is a limitation of this invention.

Still other compositions of this invention containing the two nucleotide sequences can be plant cell(s) or algal cell(s), such as species of the genera, including, without limitation, Blastocrithidia, Cephaleuros, Chlamydomonas, and Chlorella.

Where the cell is prokaryotic, desirable bacterial cells include *Escherichia coli, Bacillus subtilis, Salmonella typhimurium*, and various species of Pseudomonas, Streptomyces, Staphylococcus and Shigella or other enterobacteria. However, eukaryotic cells are preferred.

In another embodiment, in which the nucleotide sequences of the detector compositions are RNA molecules, they may also be incorporated as RNA molecules. preferably in the form of functional viral RNAs, such as tobacco mosaic Virus. Other useful viruses that may be employed in the compositions of this invention include without limitation, vaccinia, adenoviruses, adeno-associated viruses, baculoviruses, bunyaviruses, coronaviruses, flaviviruses, hepadnaviruses, herpesviruses and herpes-like viruses, orthomyxoviruses, papovaviruses, paramyxoviruses, picornaviruses, poxviruses, rcoviruses, retroviruses, and rhabdoviruses.

The nucleotide sequences present in the cells or viruses forming the detector compositions are as described below.

1. First Nucleotide Sequence(s)

The first nucleotide sequences contain at least one ligand-dependent transcription factor, preferably under the regulatory control of a selected promoter. In one embodiment, a ligand dependent transcription factor is a nuclear receptor superfamily protein or a functional fragment thereof. In another embodiment, the ligand dependent transcription factor is a modified or synthetic protein having the transcription activating properties of a nuclear receptor superfamily protein. Members of this superfamily include, without limitation, a modified or native steroid/thyroid nuclear receptor superfamily protein, such as the ecdysone [see Yao, T. P. et al (1 993) *Nature*, 366: 476–479; Yao,. T. -P. et al, (1 992) *Cell*, 71: 63–72], the estrogen, retinoid X, progesterone, glucocorticoid, vitamin D, retinoic acid, and peroxisome proliferation receptor proteins. Still optionally, the transcription factor has a function similar to that of a steroid/thyroid nuclear receptor superfamily, but is not conventionally a member of that superfamily. Among such "optional" transcription factors are those derived from a tetracycline inducible lacoperon, an IPTG inducible receptor protein, a lactone receptor protein, and an arabinose-inducible protein.

The ligand dependent transcription factors of the first nucleotide sequences of the detector composition contain a transactivation domain, a DNA binding domain ("DBD"), and a ligand binding domain ("LBD"). Each domain may be optionally separated by a hinge region of from 50 to about 1000 nucleotides of any sequence. Preferably, the hinge region is from 100 to about 500 nucleotides. In some embodiments, the hinge region is about 200 nucleotides in length. Each domain may be a naturally occurring sequence isolated from its native source, or may be a synthetically or recombinantly constructed sequence or fragment of a native sequence which has the required function. Preferably, one or more of the three domains may be chosen from a source different than the source of the other domains so that a "chimeric" first nucleotide sequence is optimized for a selected host cell for transactivating activity, complementary binding of the ligand, and recognition of a specific response element.

a. Ligand Binding Domain

The LBD of the first nucleotide sequences binds specifically only to a marker ligand of this invention. In one embodiment, the LBD also contains a transactivation domain or transactivation function, generally as its carboxy terminal sequence, so that no separate transactivation domain is necessary. The binding of the marker ligand to the LBD triggers the binding of the DNA binding domain to said response element, which activates or suppresses the expression of the reporter gene, thereby producing or altering a signal. In one embodiment of the transcription factor, the LBD is an isolated, native ligand binding domain obtained from a steroid/thyroid nuclear receptor superfamily member, such as an LBD from the insect superfamily, e.g., from the ecdysone receptor protein. Alternatively, the LBD is a synthetic or recombinantly modified ligand binding domain or fragment of such a domain from a member of that superfamily. Still alternatively, the LBD is a completely synthetic sequence which has the function of binding only to a marker ligand identified above, and triggering the above-described sequence of events. The LBD, identified from the sources above, may be isolated, prepared synthetically or recombinantly. Such LBDs are generally from about 500 to about 1000 nucleotides in length. In some embodiments, the LBDs are about 750 nucleotides in length. Particularly preferred LBD's for this methods include the ecdysone receptor LBD and the USP. The ecdysone receptor CfEcR LBD sequence is described in R. Kothapalli el al, *Dev. Genet.*, 17(4):319–330 (1995); see also Genbank Accession No. U2953 1.

In one embodiment of this invention, a single first nucleotide sequence contains a single LBD, which binds preferentially to a single marker ligand and triggers a cascade of events resulting in a change (e.g., the production, suppression, enhancement or elimination) of a detectable signal. In another embodiment, multiple different LBDs are present in the one or more first nucleotide sequences. For example, two or more LBDs may associate (e.g., form a homodimer or a heterodimer) to generate a single transcription factor or receptor for the marker ligand.

b. DNA Binding Domain

Binding of the marker ligand in the product to the one or more LBDs of the detector composition enables the one or more DBDs of the ligand dependent transcription factors to bind to the response element of the second nucleotide sequence in an activated form, thus resulting in a change (e.g., expression or suppression) of the exogenous reporter gene. In one embodiment of the transcription factor, the DBD is an isolated, native DNA binding domain obtained from a steroid/thyroid nuclear receptor superfamily member, such as a DBD from the insect superfamily, e.g., from the ecdysone receptor protein. Alternatively, the DBD is a synthetic or recombinantly modified DNA binding domain or fragment of such a domain from a member of that superfamily. Still alternatively, the DBD may be a DNA binding domain from another transcription factor. The DBD may be a DNA binding domain of a yeast cell, e.g., the GAL4 DBD or a DNA binding domain from a virus or a DNA binding domain from a plant cell. Other DNA binding domains which may be used as the DBD in the nucleotide sequences of this invention include the DNA binding domain of LexA or a DNA binding domain from a bacterial LacZ gene. Still other selections for this domain include an artificial zinc finger region. Still alternatively, the DBD is a completely synthetic sequence which, in the presence of marker ligand binding to the LBD, mediates the above-described sequence of events. Synthetic or recombinant analogs, combinations or modifications of any of the above sources of native DBDs may also be included as the DBD of the present invention.

In one embodiment, a single first nucleotide sequence contains a single DBD. In another embodiment one or more first nucleotide sequences contain more than one DBD. The DBD may be heterologous to the one or more LBDs in the one or more first nucleotide sequences. Alternatively, the DBD may be homologous to the LBD(s). Still alternatively, where two or more DBDs are present in the first nulceotide sequences, the DBDs may be the same or different DBDs. The DBD domain may be either native, modified, or chimeras of different DNA binding domains of heterologous receptor proteins. The DBD, identified from the sources above, may be isolated, prepared synthetically or recombinantly. Such DBDs are preferably from about 100 to about 1000 nucleotides in length. In one embodiment, the DBD domain is about 750 nucleotides in length. As one example, an ecdysone-derived DBD is characterized by the presence of two cysteine zinc fingers between which are two amino acid motifs, the P-box and the D-box, which confer specificity for ecdysone response elements. One particularly preferred DBD for this method is the CtEcR DBD, described in R. Kothapalli et al, *Dev. Genet.*, 17(4):3) 19–330 (1995): see also Genbank Accession No. U2953 1. Still other DBD sequences are known in the art.

C. Transactivation domain

The transactivation domain of the ligand dependent transcription factor amplifies a conformational change in the ligand dependent transcription factor, when the marker ligand in the product binds to the LBD in the detector composition. The transactivation domain may be the carboxy terminal sequence of an LBD), which supplies an activation function. Alternatively, the transactivation domain may be a sequence independent of the LBD. One or more transactivation domains may be present on one or more of the first nucleotide sequences. The transactivation domain may be a native, modified, or chimera of different transactivation domains of heterologous receptor proteins. Useful transactivation domains may be derived from a steroid/thyroid hormone nuclear receptor activation domain, a synthetic or chimeric activation domain, a polyglutamine activation domain, a basic or an acidic amino acid activation domain, a viral activation domain, a plant virus activation domain, or the VP16, GAL4, NF-kB, or BP64 activation domains. Similarly, such domains may be prepared by modifying any of the above domains, or by employing a fragment of any of the activation domains. In the first nucleotide sequence of this invention, more than one activation domain may be employed to increase the strength of activation.

A useful transactivation domain is generally a nucleotide sequence from about 16 to about 500 nucleotides in length. Preferably, more than one activation domain is employed in the first nucleotide sequence to increase the strength of activation. Transactivation domains, identified from the sources above, may be isolated, prepared synthetically or recombinantly. Particularly preferred transactivation domains for use in the method of this invention are that of VP 16, disclosed in P. E. Pellett el al Proc. Natl. Acad. Sci., USA, 82(17):5870–5874 (1985), as well as others known to those of skill in the art. See, also Swiss Prot. Accession No. PO04486 for the sequence of the VP16 transactivation domain.

d. The Promoler

The first nucleotide sequences also optionally contain a promoter which regulates the expression of at least one of the ligand dependent transcription factors in the selected cell or virus. In the method of this invention, one of skill in the art may readily select the promoter used to drive the expression of the ligand dependent transcription factor, according to a desired end result, i.e., to control the timing and location of expression. The term "promoter" means a specific nucleotide sequence recognized by RNA polymerase. The promoter sequence is the site at which transcription can be specifically initiated under proper conditions. A wide number of promoters may be selected to regulate expression of the transcription factor of the first nucleotide sequence, e.g., constitutive promoters. inducibly regulated promoters, tissue-specific promoters (expressed only in a particular type of cells) or promoters specific to certain developmental states of an organism.

However, preferably, the promoter for the first nucleotide sequence(s) is a constitutive promoter. Examples of constitutive promoters which may be selected include, without limitation, the retroviral Rous sarcoma virus LTR promoter, the cytomegalovirus promoter, the SV40 promoter, the dihydrofolate reductase promoter, the á-actin promoter, the phosphoglycerol kinase promoter, the EFI a promoter, the T7 polymerase promoter, the ecdysone insect promoter, the skeletal a-actin promoter, the myosin light chain 2A promoter, the dystrophin promoter, the muscle creatine kinase promoter, synthetic muscle promoters, the liver promoter, the hepatitis B virus core promoter, the alpha-fetoprotein promoter, the actin promoter, the IEI promoter, the IR2 and other baculovirus promoters, the HSP70 promoter, the 35S plant promoter, the CSV plant promoter, the yeast GAL1 promoter, the yeast ADHI promoter, and the yeast MET25 promoter. A presently preferred promoter is the baculovirus IEI promoter present in the sequence of AcMNPV described in M. D. Ayres et al, Virol., 202(2):586–605 (1994); see also Genbank Accession No. NC001623. Other promoter sequences may be selected from among those sequences known in the art.

Preferably in the first nucleotide sequence(s) the promoter is located 5' to the LBD, which is located 5' to the DBD, which is located 5' to the transactivation domain. These domains may be linked directly to each other by fusing the 3' nucleotide of the promoter to the 5' nucleotide of the LBD, and the 3' nucleotide of the LBD to the 5' nucleotide of the DBD, etc. Alternatively, where the transactivation domain is a part of the LBD, the LBD is linked directly or through a spacer to only a DBD. In still another alternative, one "first" nucleotide sequence contains an LBD and DBD and another "first" nucleotide sequence contains the same LBD and DBD or a different LBD and DBD, with an optional transactivation domain, whereby the LBDs and DBDs and transactivation domains of the multiple "first" nucleotide sequences form a single transcription factor as a homodimer or heterodimer. The multiple LBD, DBD and transactivation domains may be present on a single nucleotide sequence or on multiple separate nucleotide sequences. Alternatively each of these domains is preferably separated by an optional spacer of about 16 to about 30 nucleotides. For example, from 6 to about 10 glycine amino acid residues niliy be used as the spacer, e.g., from 18 to about 30 nucleotides.

The first nucleotide sequences are desirably single-stranded DNA or RNA; alternatively, they may be double-stranded DNA or RNA. The first sequences may be prepared in the form of straight chains, but are preferably circular plasmids. In still another embodiment, one first sequence may be on one plasmid, another first sequence may be on the same plasmid or on a different plasmid; and the second nucleotide sequence may be on yet another plasmid. Yet a further embodiment provides that the first nucleotide sequence(s) and the second nucleotide sequence are present on the same plasmid, provided that they are separated by one or more transcriptional blockers or polyA sequences. Still other embodiments of these sequences may employ sequences that have their origins in viruses, bacteriophages, and other molecules.

2. Second Nucleotide Sequence

The second nucleotide sequence of the detector composition encodes a reporter gene that is under the regulatory control of a receptor response element (e.g., native, modified or synthetic), and a second promoter.

a. Response element

The term "response element" ("RE") means one or more cis-acting DNA elements which confer responsiveness on a promoter mediated through interaction with the DBD of the ligand dependent transcription factor of the first nucleotide molecule. In the presence of a marker ligand in the product, the DBD of the first nuclueotide molecule binds to the RE of this second nucleotide molecule to initiate or suppress transcription of the downstream reporter gene and second promoter under the regulation of this response element.

The RE may be either palindromic (perfect or imperfect) in its sequence or composed of sequence motifs or half sites separated by a variable number of nucleotides. The half sites can be similar or identical and arranged as either direct or inverted repeats. The RE is preferably a receptor response element obtained from a steroid/thyroid nuclear receptor superfamily member, as identified above, or obtained from other sources as identified for the DBDs, or prepared synthetically. Particularly preferred REs for this method are a response element from GAL4, a response element from a steroid/thyroid hormone nuclear receptor, an artificial zinc finger, a LexA operon, a lac operon response element, and a synthetic or recombinantly produced response element that recognizes a synthetic DBD.

RE, identified from the sources above, may be isolated, prepared synthetically or recombinantly, and are generally from about 10 to about 40 nucleotides in length. Preferably the RE are about 12 to 36 nucleotides in length. As one specific example, DNA sequences for RE of the natural ecdysone receptor include: RRGG/TTCANTGAC/ACYY [Cherbas L., et al., (1991), Genes Dev. 5, 120–131]; AGGTCAN$_{(n)}$AGGTCA, where N$_{(n)}$ can be one or more spacer nucleotides [D'Avino P. P., et al, (1995), Mol. Cell. Endocrinol, 113, 1–9]; and GGGTTGAATGAATTT [Antoniewski C., et al, (1994). Mol. Cell Biol. 14, 4465–4474]. In addition, the response element itself can be modified or substituted with response elements for other DNA binding protein domains such as the GAL4 protein from yeast [Sadowski, et al (1988) Nature, 335: 563–564] or LexA protein from E. coli [Brent and Ptashne (1985), Cell, 43: 729–736].

b. The Reporter Gene

The reporter gene of the second nucleotide sequence is one that is capable of producing upon expression, directly or indirectly, a detectable signal. This gene may be readily selected from among a wealth of such reporters in the art. For example, the reporter gene may encode a protein or enzyme that is capable of producing an optically detectable, or calorimetric signal. The reporter gene may be a gene encoding a fluorescent or luminescent protein. Alternatively, the reporter gene may encode a protein that interacts with a substrate to produce a detectable signal. The reporter gene may cause directly or indirectly a red or blue shift in the emission or absorption spectrum of the detectable signal (e.g., UV, visible, NMR, etc). The protein encoded by the reporter gene may be an enzyme that can catalyze a detectable signal.

Several specific examples of such reporter genes include those that encode green fluorescent protein, luciferase, β-galactosidase, blue fluorescent protein, and secreted alkaline phosphatase. Preferably, the signal is generated by the reporter itself or by the interaction between the reporter and its substrate. As known by one of skill in the art, most reporter enzymes have more than one substrate. The reaction between the reporter enzyme and the substrate is a signal detectable by visual detection, microscopic detection, ultraviolet light detection, electrical detection, change in capacitance, hybridization, infrared detection, fluorescence detection and nuclear magnetic resonance. One of skill in the art may readily select from among a wide variety of known and commercially available reporter genes and substrates fitting these descriptions. See, also, the examples below.

c. The Second Promoter

The promoter of the second nucleotide sequence controls, with the response element, the expression of the reporter gene. The promoter may be the same as the promoter in the first nucleotide molecule of the detector compositions. Preferably the second promoter is a different, inducible promoter. As an inducible promoter, the second promoter regulates the inducible expression of the reporter in the selected cell and initiates or suppresses transcription of the reporter gene only in the presence of a complex formed by the marker ligand, the ligand-dependent transcription factor, and the response element. More preferably, the second promoter is inducible by the response element, e.g., an ecdysone RE.

In one embodiment, the second promoter is an RE-inducible, minimal promoter Such as the alcohol dehydrogenase minimal promoter or a synthetic TATA box. Most preferred promoters are ecdysone inducible promoters. Still other exemplary inducible promoters, include, without limitation, the zinc-inducible sheep metallothionine promoter, the dexamethasone-inducible mouse mammary tumor virus promoter, the tetracycline-repressible promoter, the tetracycline-inducible promoter, the RU486-inducible promoter, and the rapamycin-inducible promoter.

The function of the promoter is to modify the expression of the reporter gene, so as to induce a change in the detectable signal. For example, in certain embodiments, the second promoter turns "on" expression of the reporter gene. In other embodiments, the second promoter turns "off" expression of the reporter gene. In still other embodiments, the second promoters induces a change in the expression of the reporter gene, e.g., its suppresses or reduces expression or it enhances expression.

Preferably in the second nucleotide molecule the RE is located 5' to the second promoter, which is located 5' to the reporter gene. In one embodiment, the EcR RE are linked to a synthetic TATA box, which is linked to the reporter gene. These elements of the second nucleotide sequence may be linked directly 3' nucleotides to 5' nucleotides. Alternatively, each of these domains is preferably separated by all optional spacer of about 16 to about 30 nucleotides. For example, from 6 to about 10 glycine amino acid residues may be used as the spacer, e.g., from 18 to about 30 nucleotides. This second nucleotide sequence may be single-stranded RNA or DNA or double-stranded RNA or DNA. The second sequence may be prepared in the form of a straight chain, or preferably as a circular plasmid. In still another embodiment, the first sequence may be oil one plasmid, and the second nucleotide sequence may be on a another plasmid. Yet a further embodiment, provides that the first nucleotide sequence and the second nucleotide sequence are present on the same plasmid, provided that they are separated by a transcriptional blocker or polyA sequence. Still other embodiments of these sequences may employ sequences that have their origins in viruses, bacteriophages, and other molecules.

3. The Optional Cofactor

An optional part of the detector composition is a nucleotide sequence encoding a cofactor. Among the cofactors that may be useful or necessary depending upon the cell type into which the detector compositions is transfected include proteins generally known as coactivators (also termed adapters or mediators) or corepressors (also known as repressors, silencers, or silencing mediators).

Coactivators do not bind sequence-specifically to DNA and are not involved in basal transcription. A coactivator in the detector composition of this invention interacts with the ligand-dependent transcription factor to activate expression of the reporter gene. They may exert their effect on transcription activation through various mechanisms, including stimulation of DNA-binding of activators, by affecting chromatin structure, or by mediating activator-initiation complex interactions. Examples of such coactivators include RIP140, TIFI, RAP46/Bag-1, ARA70, SRC-I/NCoA-1, TIF2/ GRIP/ NCoA-2. ACTR/AIBI/RAC3/pCIP as well as the promiscuous coactivator C response element B binding protein, CBP/p300. For review, see C. K. Glass et al, *Curr. Opin. Cell Biol.* 9:222–232 (1997).

Corepressors may be required to effectively inhibit transcriptional activation in the absence of marker ligand. A corepressor in the detector composition of this invention interacts with the ligand-dependent transcription factor to repress expression of the reporter gene. These corepressors may interact with the unliganded ecdysone receptor to silence the activity at the response element. Current evidence suggests that binding of ligand changes the conformation of the receptor, which results in release of the corepressor and recruitment of the above described coactivators, thereby abolishing their silencing activity. Examples of corepressors include N-CoR and SMRT. For a review, see K. B. Horwitz et al. *Mol Endocrinol.*, 10:1167–1177 (1996).

In the absence of such cofactors endogenous within the cell to be transfected with the detector composition, a nucleotide sequence encoding one or more cofactors may be added exogenously to the cell as part of the detector composition. In one embodiment, a sequence encoding a cofactor may be included as part of a first or second nucleotide sequence of the detector composition. The cofactor may be placed under the control of a regulated or unregulated promoter (constitutive or inducible, as described above) or the nucleotide sequence may be engineered to be expressed by the first or second promoters described above. In another embodiment, the cofactor sequence may be placed on a separate "third" nucleotide sequence, e.g., on a separate straight chain or circular plasmid. As yet a third alternative, a selected cofactor protein may be added to the product or portion or extract of the product as a separate step in the method described herein.

4. Preparation of the Detector Compositions

Once the individual component domains and regions of the first and second nucleotide molecules (and optional third nucleotide molecule or sequence) are selected as discussed above, the nucleotide sequences useful in the methods of the invention may be prepared conventionally by resort to known chemical synthesis techniques, e.g., solid-phase chemical synthesis, such as described by Merrifield, *J. Amer. Chem. Soc.*, 85:2149–2154 (1963), and J. Stuart and J. Young, *Solid Phase Peptide Synthelia*, Pierce Chemical Company, Rockford, IL (1984), or detailed in the examples below. Alternatively, the nucleotide sequences useful in the method of this invention may be prepared and assembled by known recombinant DNA techniques and genetic engineering techniques, such as polymerase chain reaction, by cloning and expressing within a host microorganism or cell a DNA fragment carrying the above-identified nucleic acid sequences, etc. [See. e.g., Sambrook et al., Molecular Cloning. A Laboratory Manual., 2d Edit., Cold Spring Harbor Laboratory, New York (1989); Ausubel et al. (1997), Current Protocols in Molecular Biology, John Wiley & Sons, N.Y.]. These first and second molecules may be separate straight chain or circular nucleotide constructs. Alternatively, they may be circular plasmids. Still alternatively, they may be located on a single molecule. As another alternative, two or more proteins made from first nucleotide sequences may associate to form homodimers or heterodimers to generate a single transcription factor.

Once prepared, these molecules may be introduced into a selected cell by any conventional means, such as, for example, transfection, electroporation, liposome delivery, membrane fusion techniques, high velocity DNA-coated pellets, viral infection and protoplast fusion. Alternatively, if the molecules are prepared as RNA molecules, they may be designed as part of a selected virus by conventional recombinant techniques. For insect and plant cells only a first nucleotide sequence containing an LBD, DBD and transactivation domain and a second nucleotide sequence may be desired to perform this method. For mammalian cells and yeast cells, at least two "first" nucleotide sequences and a second nucleotide sequence may be desired, optionally with a cofactor, to perform this method.

It is preferred for ease of use of the present inventions that the cells or viruses of the detector compositions be prepared in live, unfrozen or live, lyoplilized form. Any of the above-identified cells, once transfected with the first and second nucleotide molecules, may be lyophilized by conventional means, such as those taught in conventional texts.

Even more preferably, the lyophilized cell or viral detector composition is immobilized on a solid support. Among suitable solid supports include microcells, microcapsules, microtiter plates, beads, and biochips. Useful supports include those described in International Patent Publication WO99/2735 1. published Jun. 3, 1999; or International Patent Publication WO99/27140, published Jun. 3, 1999; U. S. Pat. No. 6,096,273; International Patent Publication WO00/14197, published Mar. 16. 2000, among others. Such solid supports for immobilizing the cells or lyophilized cells of the detector compositions may be selected from among the many known types available commercially; and methods for adhering the cells or viruses to the supports are provided by the manufacturers of the supports. In yet another embodiment, the support may be an adhesive, e.g., for application to solid products.

D. Performance of the Method

The method of the present invention thus relies on the presence of a marker ligand in or on a selected product of the present invention. To detect the presence or quantity the marker ligand in the product, the product is contacted with one or more detector compositions as defined above. If the marker ligand is applied to the solid product, rather than a liquid product, it may be extracted from the solid product. For ease of use, it is preferred that the detector composition comprise an immobilized transfected cell or RNA virus as described above. For example, when a sample of product is placed on a detector composition immobilized on a biochip, the marker ligand binds preferentially to the LBD in the immobilized cell. This binding causes a conformational change in the ligand dependent transcription factor which causes the DBD to complex with the RE on the second nucleotide molecule. The complex formed between the DBD and the RE activates the second promoter, which modulates the expression of the exogenous reporter gene.

The order in which the various components bind to each other, that is, marker ligand to LBD-DBD-transactivation domain sequence and DBD to response element, is not critical. However, the presence of the marker ligand is absolutely required to either turn on expression of the reporter gene or turn off expression of a reporter gene or change the expression of the reporter gene, thereby creating a detectable signal or detectable change in the signal indicative of the presence of the marker ligand. If no marker ligand is present in the product, no change of signal is detectable.

E. A Detection Kit

The components of this method are readily adaptable into a kit that contains one or more detector compositions suitable for detecting the marker ligand in a liquid or solid product, suitable vessels for containing sample and/or a plurality of detector compositions of the invention in an environment suitable for preserving the detectable properties of the signals generated by the reporter gene or reporter gene system, and/or suitable substrates for interaction with the reporter gene product to produce a detectable signal. The kit of the present invention can contain either the same or different detector compositions, whereby a plurality of samples can be examined with the same detector compositions or with multiple detector compositions. These kits can additionally contain reagents necessary to culture the cells, if necessary; and/or reagents necessary to reactivate the Lyophilized cells or lysates; instructions for performing a detection assay, substrates to which the detector composition has been pre-adsorbed in a lyophilized state, diluents and buffers, indicator charts for signal comparisons, disposable gloves, decontamination instructions, applicator sticks or containers, and sample preparator cups. For convenience, it is preferable, to provide frozen, lyophilized or otherwise preserved cells which, after reactivation, express the detector compositions of the invention. The kits of the invention can contain intact cells constitutive expressing the reporter proteins of the invention or cells only expressing the reporter protein alter induction or expressing as long as no inhibitor is added. Respective inducers or inhibitors are preferably also included in these kits. Further, the kits preferably include the solutions required for reactivating preserved expression systems. The kits preferably also contain necessary buffer substances or culture media, as far as this is required due to the expression system used.

Kits of the invention are useful for the rapid screening of a plurality of samples for the presence or absence of marker ligand. Use according to the invention, therefore, is in accordance with the methods of the invention already discussed in detail above, whereby the use of the kits of the invention enable a user to carry out determination of product source or adulteration in a simple and rapid manner, with the kit of the invention preferably providing him with all components required.

F. The Examples

The following examples illustrate several embodiments of the methods and compositions of this invention. These examples are illustrative only, and do not limit the scope of the present invention.

EXAMPLE 1

THE EcR GENE SWITCH

An embodiment of the ecdysone gene switch is prepared as a receptor plasmid (the first nucleotide molecule described above) and a reporter plasmid (the second nucleotide molecule described above).

The receptor plasmid pIEIVPI16CfEcRCDEF contained CfIEcR CDEF domains fused to the VP16 activation domain and expressed under the baculovirus IEI promoter. This plasmid was constructed in two steps. To construct vector pIEIVP16, the IEI promoter region of AcMNPV (described in Ayres et al, cited above) was amplified using primers tagged with Ndel and Bglll restriction enzyme sties. The amplified product was cloned into plasmid vector containing the VP16 activation domain (described in Pellett et al, cited above), and multiple cloning sites, followed by an SV40 polyA signal. CtlEcR CDEF domains (described in Kothapalli et al, cited above) were amplified using primers tagged with BamHI and Xbal. The amplified CfEcRCDEF was then cloned into the pIEIVP 16 vector.

The reporter plasmid pMK43.2 contained the 6X ecdysone response elements from the heat shock protein 27 gene, as described in Riddihough and Pelham, *EMBO J.*. 6:3729–3734 (1987), cloned upstream to an alcohol dehydrogenase minimal promoter and an E. coli β-galactosidase reporter gene. The construction of that plasmid is described in M. R. Koelle et al, *Cell,* 67:59–77 (1991).

The gene switch operates as follows when the two plasmids are transfected into a host cell. The EcR protein, which in the receptor plasmid described above is produced constitutively by the baculovirus IEI promoter, is expressed in the cytoplasm of the selected host cell in an inactive form. In an alternative embodiment, the EcR protein can be placed under the control of a tissue-specific inducible or developmentally regulated promoter to control the timing and location of EcR expression in the host. The EcR protein migrates to the cell nucleus and binds to a specific DNA sequence, referred to as the Response Element, which is present in the reporter plasmid described above. The Response Element is a unique DNA sequence that is not naturally found in the host's DNA and is uniquely recognized by the EcR protein. The Response Element is functionally linked to the regulated gene of interest, which in this embodiment is the reporter gene β-galactosidase.

When the cell is contacted by marker ligands, e.g., in a sample which is exposed to the cell in one of the assays of Example 3 or 4, the marker ligands bind to and activate the EcR receptor to "switch on" expression of the p-galactosidase gene and thus produce the protein encoded by that gene. The assays described below are designed to allow the identification and measurement of that reporter gene.

EXAMPLE 2

PREPARATION OF MARKED SOLUTIONS

To a 100 ml volumetric flask was added 1.0166g of the marker ligand. methoxyfenoxide (N'-tert-butyl-N'-(3 ,5-dimethylbenzoyl)-3-methoxy-2-methylbenzohydrazide). The solution was diluted to 100 mL volume with absolute ethanol, resulting in Solution A. One milliliter of Solution A contains approximately 10 mg of marker ligand.

Solution B was prepared by adding to a 100 ml volumetric flask 10 ml (±0.04 mL) of Solution A above. The resulting solutions were each diluted to 100 mL volume with absolute ethanol. The resulting Solution B contained approximately I mg marker ligand.

Solution C was prepared by adding to a 100 ml volumetric flask 10 mL (±0.04 mL) of Solution B. The solution was diluted to 100 mL volume with absolute ethanol. One ml of the resulting Solution C contains approximately 0.1 mg marker ligand.

To prepare sample solutions for testing in the yeast and insect assays below, 1 mL (±0.12 mL) of stock solution A, B, or C was added to approximately 100 g of gasoline or vodka, as summarized in Table I below:

TABLE 1

| Sample # | Stock Solution | Dilution with gasoline or vodka | Concentration mg/ml |
|---|---|---|---|
| 1 | A | 100.07 g gasoline | 6.95 |
| 2 | B | 100.08 g gasoline | 0.69 |
| 3 | C | 100.01 g gasoline | 0.07 |
| 4 | A | 100.04 g vodka | 11.67 |
| 5 | B | 100.06 g vodka | 1.17 |
| 6 | C | 100.03 g vodka | 0.12 |

After the samples in Table I were diluted 1 to 100 in acetonlitrile/water (1/1), the concentration of the marker ligand in each gasoline and vodka sample was quantified by liquid chromatography/mass spectrometry (LC/MS) on a HP1000-VG platform. LC involves gradient separation on a 3×50mm C-18 column (Polaris Metachem) using an injection volume of 25 µL. The MS was in signal ion monitoring mode providing specific detection of marker ligand molecular ions. All HPLC standards were prepared in acetonitrile/water (1/1). Quantification was performed comparing analyte concentration (area) and five standard concentrations (area) which were analyzed before and after each marker ligand set (A,B, and C for gasoline or vodka). The results are summarized in Table 2.

TABLE 2

| Sample | Type | Std Conc. µg/ml | Retention Time, minutes | Area | Response | µg/ml |
|---|---|---|---|---|---|---|
| Std | Standard | 0.012 | 4.646 | 1211 | 1210.613 | 0.0119 |
| Std | Standard | 0.12 | 4.646 | 11145 | 11144.99 | 0.1099 |
| std | Standard | 1.2 | 4.646 | 120026 | 120026.1 | 1.2085 |
| std | Standard | 12 | 4.646 | 940122 | 940122.4 | 11.9851 |
| wash | Blank | | 4.863 | 14 | 13.547 | 0.0001 |
| 1 | Analyte | | 4.646 | 76515 | 76514.81 | 0.7638 |
| 2 | Analyte | | 4.61 | 8257 | 8256.889 | 0.0813 |
| 3 | Analyte | | 4.61 | 916 | 915.831 | 0.009 |
| 4 | Analyte | | 4.646 | 129204 | 129203.8 | 1.3033 |
| 5 | Analyte | | 4.646 | 14591 | 14590.56 | 0.1439 |
| 6 | Analyte | | 4.646 | 1545 | 1544.863 | 0.0152 |
| wash | Blank | | 4.61 | 10 | 9.863 | 0.0001 |
| std | Standard | 0.012 | 4.646 | 1222 | 1221.55 | 0.012 |
| std | Standard | 0.12 | 4.646 | 11546 | 11545.91 | 0.1138 |
| std | Standard | 1.2 | 4.646 | 120204 | 120203.5 | 1.2103 |
| std | Standard | 12 | 4.61 | 941603 | 941603.3 | 12.0119 |

These results demonstrate that conventional analytical chemical detection (e.g., chromatographic methods) can be used to detect the presence of marker ligand in samples of gasoline and vodka.

EXAMPLE 3

INSECT CELL-BASED MARKER LIGAND ASSAY

An insect cell line, BRL-AG2, was derived from cotton boll weevil, *Anthomus grandis* as described in Stiles et al, *In Vitro Cell Dev. Biol.*, 28A:355–363 (1992). Another insect cell line L57 was prepared as a *Drosophila melanogaster* Kc cell line modified to silence the expression of the ecdysone receptor. Each of these insect cell lines was transfected with the receptor plasmid and reporter plasmid described in Example 1 above.

In the insect cell-based marker ligand assay, 200,000 of the transfected BRL-AG2 cells or the L57 cells described above were distributed per well of 48-well plates. 0.5 µL of either a negative control, e.g., DMSO, or a marked product (vodka or gasoline) of Example 2 was added to the cells. The cells were maintained in the medium containing the marker ligand solutions of Example 2 or a positive control (i.e., methoxyfenoxide in alcohol) or a negative control (alcohol only) for 48 hours at 25° C. The cells were harvested and resuspended in reporter lysis buffer (Promega Corporation, Madison., Wis.) for 15 minutes. A 10 µL aliquot of the buffer containing the resuspended cells was assayed for β-galactosidase activity using Galacto-Star™ chemiluminescent reporter gene assay system (Tropix Corporation, Bedford, Mass.). Fold induction was calculated by dividing relative light units (RLUs) in the presence of the marker ligand with the RLUs in the absence of the marker ligand.

The results are tabulated in Tables 3 and 4 below.

TABLE 3

Detection of Markers in Vodka:

| Concentration of Marker (mg/ml) | BRL-AG2 Cells (Fold Induction) | L57 Cells (Fold Induction) |
|---|---|---|
| 0 | 1 | 1 |
| 0.00007 | 151 | 27 |
| 0.00069 | 182 | 46 |
| 0.00695 | 202 | 63 |

TABLE 4

Detection of Markers in Gasoline:

| Concentration of Marker (mg/ml) | BRL-AG2 (Fold Induction) | L57 Cells (Fold Induction) |
|---|---|---|
| 0 | 1 | 1 |
| 0.00012 | 16 | 1 |
| 0.0012 | 21 | 23 |
| 0.012 | 31 | 30 |

The cells appeared healthy even at 50 µLs vodka or gasoline. There is an approximately 20–50X induction of reporter activity by marked products. The marked product containing of 0.5 µL per mL of marker ligand is sufficient to observe significant change in reporter activity. These results demonstrate an increased sensitivity of at least 10× for marker ligand vs. the chemical methods of Example 3. The marker solutions could be further diluted in the biological assay because the biological assay reached saturation at the lowest concentration tested. The biological assay results mimic the chemical analysis in that the gasoline samples show a lower concentration of marker ligand. This indication may be due to error in calculating the marker ligand concentration in the gasoline samples.

All references cited above are incorporated herein by referenece. Numerous modifications and variations of the present invention are included in the above-identified specification and are expected to be obvious to one of skill in the art. Such modifications and alterations to the compositions and processes of the present invention are believed to be encompassed in the scope of the claims appended hereto.

What is claimed is:

1. A method of marking a product for identification, said method comprising the steps of:
   (a) introducing into or onto said product a marker ligand in a concentration detectable by binding with a detector composition;
   (b) contacting said product, a portion of said product or an extract of said product with said detector composition comprising
      (1) one or more first nucleotide sequences encoding one or more natural or synthetic ligand-dependent transcription factors, wherein said factors comprise at least one ligand binding domain, at least one DNA binding domain and at least one transactivation domain; and
      (2) a second nucleotide sequence encoding a reporter gene under the regulatory control of a receptor response element or a modified or synthetic response element, and a second promoter;
   wherein the interaction between said marker ligand and said at least one ligand binding domain of said detector composition is highly specific and induces a change in the expression of said reporter gene, said change producing a detectable signal identifying the presence of said ligand in said product, and (c) detecting said detectable signal by a detection means, whereby said detectable signal indicates the presence of said marker ligand in said product.

2. The method according to claim 1, wherein said transcription factor is under the regulatory control of a first promoter.

3. The method according to claim 1, wherein said transactivation domain is a carboxy terminal portion of a ligand binding domain that enhances activation.

4. The method according to claim 1, wherein said transactivation domain is a sequence independent of said ligand binding domain.

5. The method according to claim 1, wherein said composition further comprises a third nucleotide sequence encoding a coactivator or corepressor that interacts with the ligand-dependent transcription factor to activate or repress expression of said reporter gene.

6. The method according to claim 1, wherein said product is contacted with a coactivator or repressor protein that interacts with the ligand-dependent transcription factor to activate or repress expression of said reporter gene.

7. The method according to claim 1, wherein said ligand dependent transcription factor is a nuclear receptor superfamily protein or functional fragment thereof.

8. The method according to claim 1, wherein said ligand dependent transcription factor is a modified or synthetic protein having the transcription activating properties of a nuclear receptor superfamily protein.

9. The method according to claim 7 wherein said factor is a modified insect nuclear receptor superfamily protein.

10. The method according to claim 7, wherein said factor is selected from the group consisting of ecdysone, estrogen, retinoid X, progesterone, glucocorticoid, vitamin D, retinoic acid, and peroxisome proliferation receptor [protein] proteins.

11. The method according to claim 1, wherein said factor is selected from the group consisting of a tetracycline inducible lac operon, an IPTG inducible receptor protein, a lactone receptor protein, and an arabinose-inducible proteins.

12. The method according to claim 1, wherein said composition is a cell comprising said first nucleotide sequence and said second nucleotide sequence.

13. The method according to claim 12, wherein said cell is a eukaryotic cell.

14. The method according to claim 12, wherein said cell is a prokaryotic cell.

15. The method according to claim 12, wherein said cell is immobilized on a solid support.

16. The method according to claim 1, wherein said binding of said marker ligand to said ligand binding domain triggers the binding of the DNA binding domain to said response element, wherein said bound response element activates or suppresses the expression of said reporter gene.

17. The method according to claim 1, wherein said composition contains multiple different ligand binding domains, which associate to provide a single receptor.

18. The method according to claim 1, wherein said composition contains a single ligand binding domain.

19. The method according to claim 1, wherein said ligand binding domain is selected from the group consisting of the ligand binding domain from a steroid/thyroid nuclear receptor superfamily member, a synthetic or recombinantly modified domain thereof; a fragment of said domain, and an analog thereof.

20. The method according to claim 1, wherein said DNA binding domain mediates binding of said ligand-dependent transcription factor to said response element of said second nucleotide sequence.

21. The method according to claim 20, wherein said DNA binding domain is heterologous to said ligand binding domain.

22. The method according to claim 20, wherein said DNA binding, domain is selected from the group consisting of a DNA binding domain of GAL4, a DNA binding domain of LexA, a DNA binding domain from a transcription factor; a DNA binding domain from a steroid/thyroid nuclear receptor superfamily member, a DNA binding domain from a bacterial LacZ, a DNA binding domain from a yeast cell, a DNA binding domain from a plant cell, a DNA binding domain from a virus, an artificial zinc finger region a synthetic or recombinant analog, combination or modification thereof.

23. The method according to claim 1, wherein said transactivation domain amplifies a conformational change in the ligand dependent transcription factor when the ligand binds to said ligand binding domain.

24. The method according to claim 23, wherein said transactivation domain is selected from the group consisting of a steroid/thyroid hormone nuclear receptor activation domain, a synthetic or chimeric activation domain, a polyglutamine activation domain, basic or acidic amino acid activation domain, a viral activation domain, a plant virus activation domain, or the VP16, GAL4, NF-kB, or BP64 activation domain, a modified activation domain, a fragment of any of said activation domains and a modification thereof.

25. The method according to claim 24, wherein more than one activation domain is employed to increase the strength of activation.

26. The method according to claim 1, wherein said response element is selected from the group consisting of a response element from GAL4, a response element from a steroid/thyroid hormone nuclear receptor, an artificial zinc finger-. a LexA operoni, a lac operon response element, and a synthetic or recombinantly produced response element that recognizes a DNA binding domain.

27. The method according to claim 1, wherein said first promoter regulates the expression of said factor in a selected host cell or virus.

28. The method according to claim 2, wherein said first promoter is a constitutive promoter.

29. The method according to claim 1, wherein said second promoter regulates the inducible expression of said reporter in the selected host cell and initiates or suppresses transcription of said reporter gene only in the presence of a complex formed by the marker ligand, the ligand-dependent transcription factor, and said response element.

30. The method according to claim 29 wherein said first and second promoter are the same.

31. The method according to claim 30, wherein said second promoter is an inducible promoter.

32. The method according to claim 1, wherein the change in expression of said reporter gene is detectable by a method selected from the group consisting of visual detection, microscopic detection, ultraviolet light detection, electrical detection, change in capacitance, hybridization, infrared detection, fluorescence detection and nuclear magnetic resonance.

33. The method according to claim 32, wherein said reporter gene is a gene encoding a fluorescent or luminescent protein.

34. The method according to claim 32, wherein said reporter gene encodes a protein that interacts with a substrate to produce a detectable signal.

35. The method according to claim 32, wherein said reporter gene causes directly or indirectly a shift in the emission spectrum of said detectable signal.

36. The method according to claim 34, wherein said protein is all enzyme that can catalyze a detectable signal.

37. The method according to claim 1, wherein said marker ligand is a molecule that specifically binds to said ligand binding domain.

38. The method according to claim 35, wherein said ligand is a synthetic chemical compound.

39. The method according to claim 37, wherein said marker ligand is selected from the group consisting of ponasteroneA, muristerone A, an alkylhydrazine, N,N'-diacylhydrazine, an N-substituted-N, N' diacylhydrazine, an N-substituted-N,N -disubstituted hydrazine, a dibenzoylalkyl cyanohydrazine, an N-alkyl-N,N'-diaroyl hydrazine, an N-acyl-N- alkyl-N'-aroylhydrazine, a 3,5-di-tert-butyl-r-hydroxy-N-isobutyl-benzaide, and an 8–0- acetylharpagide.

40. The method according to claim 1, wherein said product is selected from the group consisting of a liquid, a solid, a dispersion, an emulsion, and a latex.

41. The method according to claim 40, wherein said marker ligand is admixed directly into said product.

42. The method according to claim 40, wherein the product is a solid and the marker ligand is applied to the surface of the product, or to a tag or packagingassociated with the product.

43. The method according to claim 40, wherein said ligand is present in said liquid product at a concentration of between 0.1 to 10 parts per billion.

44. The method according to claim 40, wherein said ligand is present in said solid product at a concentration of between 10 to 500 parts per billion.

* * * * *